(12) United States Patent
Agut et al.

(10) Patent No.: US 6,926,899 B2
(45) Date of Patent: Aug. 9, 2005

(54) GLYCOPROTEIN PEPTIDE OF THE HUMAN HERPESVIRUS-7 FOR USE IN PARTICULAR IN AN ELISA SEROLOGIC TEST

(75) Inventors: Henri Agut, Paris (FR); Michael Franti, La Garenne-Colombes (FR)

(73) Assignee: Universite Pierre et Marie Curie (Paris VI), Paris (FR)

( * ) Notice: Subject to any disclaimer, the term of this patent is extended or adjusted under 35 U.S.C. 154(b) by 0 days.

(21) Appl. No.: 10/460,503

(22) Filed: Jun. 13, 2003

(65) Prior Publication Data

US 2004/0091852 A1 May 13, 2004

Related U.S. Application Data

(63) Continuation of application No. PCT/FR01/04010, filed on Dec. 14, 2001.

(30) Foreign Application Priority Data

Dec. 15, 2000 (FR) .............................................. 00 16431

(51) Int. Cl.[7] ............................................. A61K 39/245
(52) U.S. Cl. .................................. 424/229.1; 424/204.1; 530/300; 435/6; 536/23.72
(58) Field of Search ............................ 424/229.1, 204.1; 536/23.72; 530/300; 435/6

(56) References Cited

FOREIGN PATENT DOCUMENTS

WO    WO 99/02554 A2    1/1999

OTHER PUBLICATIONS

Marion, Oriano et al.,Int.J. Peptide Protein Res., vol. 36, pp. 374–380 (1990).
Franti, Michael et al., Journal of Virology, vol. 73, No. 11, pp. 9655–9658 (1999).
Franti, Michael et al., Journal of Virology, vol. 72, No. 11, pp. 8725–8730 (1998).
Hata, Atsuki et al., Virus Res., vol. 46, Abstract No. 126–128384.

*Primary Examiner*—Ali R. Salimi
(74) *Attorney, Agent, or Firm*—Birch, Stewart, Kolasch and Birch, LLP

(57) ABSTRACT

The invention concerns an immunogenic peptide comprising at least six consecutive amino acids of a hydrophilic region of the glycoprotein B (gB) of the human herpesvirus-7 (HIV-7), and reacting specifically with antibodies directed against HHV-7, and diagnosis kit containing it.

8 Claims, 9 Drawing Sheets

PEPTIDE H7                    L S S S I S V K R S E E E E Y V A Y H K D E Y V N

HHV_7 gB      P I E E V H M V N T E A R C L S S S I S V K R S E E E E Y V A Y H K D E Y V N K T L D L I P L N K K S D
(115.166)

HHV_6A gB     P V Y E A N L V N S H A Q C Y S A V A M K R P D G T V F S A F H E D N N K N N T L N L F P L N F K S I
(118.169)

HHV_6B gB     P M Y E A N L V N S R A Q C Y S A V A I K R P D G T V F S A Y H E D N N K N E T L E L F P L N F K S V
(118.169)

CMV gB        P M W E I H H I N K F A Q C Y S S S Y S – R V I G G T V F V A Y H R D S Y E N K T M Q L I P D D Y S N T
(172.222)

• HOMOLOGIC AREA HHV_7 (AT PEPTIDE H7)
▶ PIC D'HYDROPHILICITE
Ⓖ SITE POSSIBLE DE N-GLYCOSYLATION

FIG.3

SEQUENCE LISTING

<160> NUMBER OF SEQ ID NOS: 7

<210> SEQ ID NO 1
<211> LENGTH: 24
<212> TYPE: PRT
<213> ORGANISM: Human Herpesvirus 7

<400> SEQUENCE: 1

Leu Ser Ser Ile Ser Val Lys Arg Ser Glu Glu Glu Tyr Val Ala
1               5                  10                 15

Tyr His Lys Asp Glu Tyr Val Asn
            20

<210> SEQ ID NO 2
<211> LENGTH: 6
<212> TYPE: PRT
<213> ORGANISM: Human Herpesvirus 7

<400> SEQUENCE: 2

Arg Ser Glu Glu Glu Glu
1               5

<210> SEQ ID NO 3
<211> LENGTH: 12
<212> TYPE: PRT
<213> ORGANISM: Human Herpesvirus 7

<400> SEQUENCE: 3

Ser Val Lys Arg Ser Glu Glu Glu Glu Tyr Val Ala
1               5                  10

<210> SEQ ID NO 4
<211> LENGTH: 51
<212> TYPE: PRT
<213> ORGANISM: HUMAN HERPESVIRUS 7

<400> SEQUENCE: 4

Pro Ile Glu Glu Val His Met Val Asn Thr Glu Ala Arg Cys Leu Ser
1               5                  10                 15

Ser Ile Ser Val Lys Arg Ser Glu Glu Glu Tyr Val Ala Tyr His
            20                  25                 30

Lys Asp Glu Tyr Val Asn Lys Thr Leu Asp Leu Ile Pro Leu Asn Phe
        35                  40                 45

Lys Ser Asp
    50

<210> SEQ ID NO 5
<211> LENGTH: 51
<212> TYPE: PRT
<213> ORGANISM: HUMAN HERPESVIRUS 6A

<400> SEQUENCE: 5

Pro Val Tyr Glu Ala Asn Leu Val Asn Ser His Ala Gln Cys Tyr Ser
1               5                  10                 15

Ala Val Ala Met Lys Arg Pro Asp Gly Thr Val Phe Ser Ala Phe His
            20                  25                 30

Glu Asp Asn Asn Lys Asn Asn Thr Leu Asn Leu Phe Pro Leu Asn Phe
        35                  40                 45

Lys Ser Ile
    50

<210> SEQ ID NO 6
<211> LENGTH: 51
<212> TYPE: PRT
<213> ORGANISM: HUMAN HERPESVIRUS 6B

<400> SEQUENCE: 6

Pro Met Tyr Glu Ala Asn Leu Val Asn Ser Arg Ala Gln Cys Tyr Ser
1               5                  10                 15

```
                                    -continued

Ala Val Ala Ile Lys Arg Pro Asp Gly Thr Val Phe Ser Ala Tyr His
            20                  25              30

Glu Asp Asn Asn Lys Asn Glu Thr Leu Glu Leu Phe Pro Leu Asn Phe
        35                  40              45

Lys Ser Val
    50

<210> SEQ ID NO 7
<211> LENGTH: 50
<212> TYPE: PRT
<213> ORGANISM: cytomegalovirus (CMV)

<400> SEQUENCE: 7

Pro Met Trp Glu Ile His His Ile Asn Lys Phe Ala Gln Cys Tyr Ser
1               5                   10                  15

Ser Tyr Ser Arg Val Ile Gly Gly Thr Val Phe Val Ala Tyr His Arg
            20                  25                  30

Asp Ser Tyr Glu Asn Lys Thr Met Gln Leu Ile Pro Asp Tyr Ser
        35                  40                  45

Asn Thr
    50
```

GLYCOPROTEIN PEPTIDE OF THE HUMAN HERPESVIRUS-7 FOR USE IN PARTICULAR IN AN ELISA SEROLOGIC TEST

This application is a Continuation of copending PCT International Application No. PCT/FR01/04010 filed on Dec. 14, 2001, which designated the United States, and on which priority is claimed under 35 U.S.C. § 120, the application also claims priority under 35 U.S.C. § 119 to French application serial no. 0016431 filed on Dec. 15, 2000. The entire contents of which are hereby incorporated by reference.

The present invention relates to peptides from the glycoprotein B from human herpesvirus 7 (HHV-7), which can be used to carry out a serological test that is specific for HHV-7, or in pharmaceutical compositions intended to stimulate an immune response directed against HHV-7.

Human herpesvirus 7 is a β-herpesvirus (virus with a DNA envelope) discovered in 1990. The virus is widespread in the general population and produces a primary phase infection early in life and, like other herpesviruses, persists indefinitely in the latent form in the infected organism. HHV-7 is genetically close to cytomegalovirus (CMV) and to human herpesvirus 6 (HHV-6) which, especially in the case of CMV, are major pathogenic viruses. The responsibility of HHV-7 for human diseases appears to be modest from current knowledge, but its pathogenic power is far from having been explored completely. It is feared that, during immunodepression, its pathogenic power is exacerbated and gives rise to serious opportunistic infections, like other herpesviruses. In particular, this may be the case after organ transplant. The reactivation of HHV-7 may be pathogenic and may aggravate the immunodepressed condition because of the selective tropism of HHV-7 for T CD4+ lymphocytes.

Further, molecules that are active against CMV and already widely used in medical therapy (foscarnet, cidofovir, ganciclovir) are active against HHV-7. A priori, the existence of active treatments further underlines the importance of continuing studies on the detection of infections using that virus.

There is currently no completely satisfactory means on the market for the specific diagnosis of a chronic infection by HHV-7. Methods for the specific diagnosis of an infection by HHV-7 based on amplifying a portion of the viral genome by PCR using specific primers for HHV-7 have been described, for example in International patent application WO-A-97/03345. However, such methods lack sensitivity for diagnosing a chronic infection and are thus destined to detect (and possibly quantify) an active infection.

Detection of a chronic infection necessitates a serological test, which will reveal the presence or otherwise of anti-HHV-7 antibodies in the sample. Current commercially available serodiagnostic HHV-7 systems are not completely satisfactory. HHV-7 diagnosis is currently carried out using cells infected with HHV-7 as the antigen. However, the genetic proximity of other β-herpesviruses, in particular HHV-6, deleteriously affects the specificity of that type of test. Adsorption tests on antigens from cells infected with the other viruses are necessary to enhance the specificity of said tests.

Thus, determination of antigenic molecules that are genuinely specific to HHV-7 represents a significant advance in the development of a serological test that is specific for this virus and easy to carry out.

In this context, Secchiero et al described antigens for a HHV-7 protein, pp85 (WO-A-99/02554). Certain of said antigens appear to be specific to HHV-7.

However, protein pp85, coded for by the U14 gene, is a tegument phosphoprotein for which a lower specificity than that carried by the glycoproteins of the viral envelope can be expected. Further, although a specific epitope has been localized in the C-terminal portion of the protein, the peptides carrying that epitope could not be used to establish a functional ELISA test (Stefan et al, J Clin Microbiol 1999; 37: 3980–5), which remains the prime objective of HHV-7 serology. Finally, in terms of immune protection, it is conventionally recognized that the glycoproteins of the viral envelope, and in particular gB, are a better target for neutralizing antibodies than tegument proteins.

The present invention concerns peptides from HHV-7 glycoprotein B (gB).

HHV-7 gB, present on the surface of infected cells and virions, is involved in attachment and fusion of the virus to the cell surface. By analogy with the other herpesviruses, it was supposed that gB was immunogenic, giving rise to neutralizing antibodies and a cellular immune response in infected subjects. All of the results published so far corroborate this hypothesis, even though gB, an indispensable protein of the virus, doe not appear to be like the immunodominant protein as regards the reactivity of the human seric antibodies in current immunoblot tests.

The first part of the study of gB consisted of amplifying the gene for gB using a polymerase chain reaction (PCR) and analyzing the corresponding PCR products in more than 100 subjects. This study showed that the gene for gB was very stable (Franti et al, 1998 and 1999). This data agrees with a comparison of two distinct strains of HHV-7 the complete sequence of which has been published (Nicholas, 1996; Megaw et al, 1998): the nucleotide divergence between the two strains is of the order of 0.1%. However, a determination of the partial nucleotide sequence for gB in many individuals has demonstrated five critical base substitution sites with no modification to the polypeptide sequence and 6 distinct combinations of said sequences, alleles, have been described. Said alleles are very important as epidemiological markers, but their description does not cause the perfect conservation of the gB as a viral protein among all of the strains tested to be re-examined. This property constitutes a good candidate for defining antigenic reagents that can react with antibodies directed against any viral HHV-7 strain in circulation.

The present invention results from cloning the entire gene for gB and its expression in a prokaryotic expression system, colibacillus. Further, the entire gene and the N-terminal portion have been cloned and expressed in a eukaryotic expression system, baculovirus. Stable expression has been obtained in bacteria, as well as stable expression with cleavage of the precursor protein in the baculovirus system. Expression at the surface of SF21 insect cells infected with recombinant baculoviruses appears to be close to that of natural gB. This production of recombinant protein, after transfer of the protein to a nitrocellulose membrane, has allowed the reactivity of a battery of eight different human serums seropositive for HHV-7 to be tested using a Western blot technique.

A first series of experiments led to the following conclusions: (i) specific antibodies directed against the recombinant gB exist in the eight serums tested; (ii) the reactivity of the antibodies directed against said surface glycoprotein is directed against the N-terminal portion of the gB which produces the same reaction profile as the entire protein. This confirms the hypothesis that gB induces antibodies in infected subjects and that partial forms of recombinant gB, allow said antibodies to be detected. However, the results are spoiled by the presence of unwanted bands, probably related to non specific reactivity phenomena, and the Western blot technique is not really suitable to large scale use.

In order to overcome these problems, the authors of the present invention undertook to define and synthesize a peptide localized in the N-terminal region of gB. Said peptide had to have the following two characteristics: (i) the peptide must be derived from a highly hydrophilic region of gB, which can interact with an antibody; (ii) the peptide must have a very low homology with the gB of the two other human β-herpesviruses, HHV-6 (which includes two variants, HHV-6A and HHV-6B) and CMV, to avoid cross serological reactions. The spotlight fell on a peptide containing 24 amino acids, corresponding to amino acids 129–152 of gB, located in the N-terminal region and defined by the peptide sequence:

Peptide H7GB 129–152

Leu-Ser-Ser- Ile-Ser-Val-Lys-Arg-Ser-Glu-Glu-Glu-Glu-Tyr-Val-Ala-Tyr-His-Lys-Asp-Glu-Tyr-Val-Asn (LSSISVKRSEEEEYVAYHKDEYVN) (SEQ ID NO: 1).

Reference should now be made to FIGS. 1 to 3 in order to define and identify the selection of the peptide in the protein.

FIG. 3 shows the alignment of the protein sequences of the gB of HHV-7, HHV-6A, HHV-6B and CMV (SEQ ID NOS: 4–7), in the region of the H7GB 129–152 peptide (SEQ ID NO: 1) (shown on the first line).

Figure 1A:
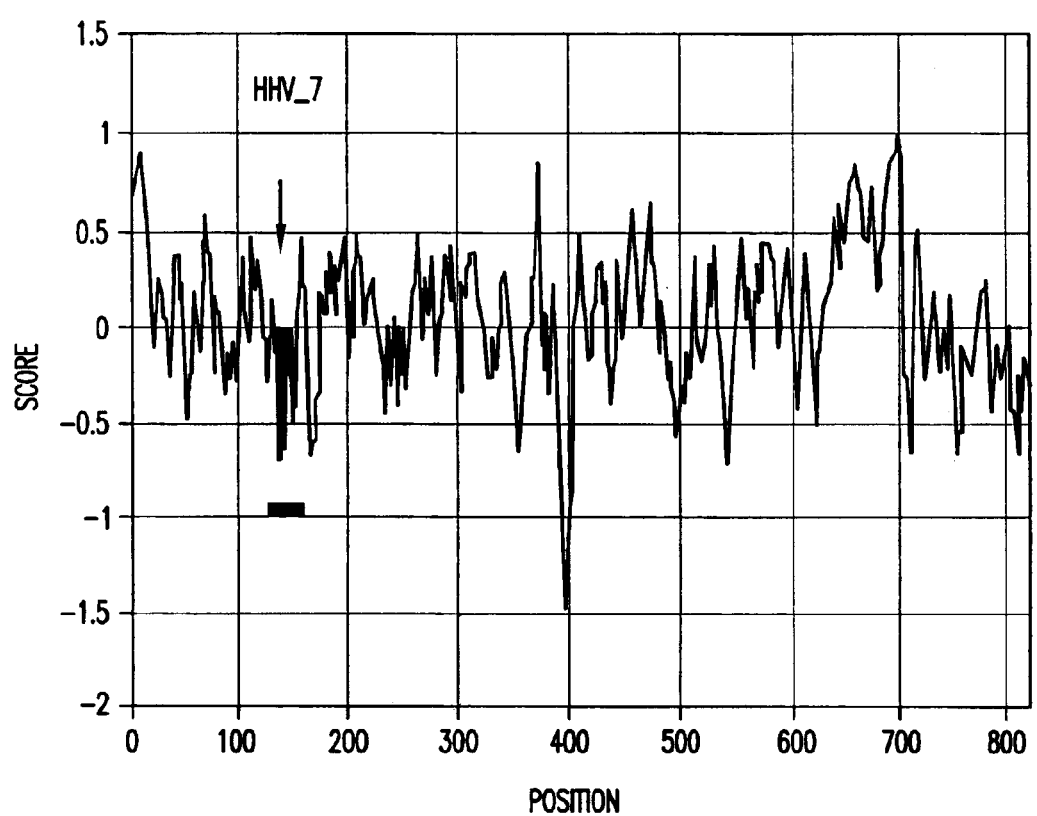
FIG. 1 shows the hydrophilicity curves for HHV-7 gB (1A), HHV-6A (1B), HHV-6B (1C) and CMV (1D), on which the region corresponding to the region exposed to HHV-7 gB is indicated by an arrow and the H7GB 129–152 peptide is shown as a black line.
Figure 1B:
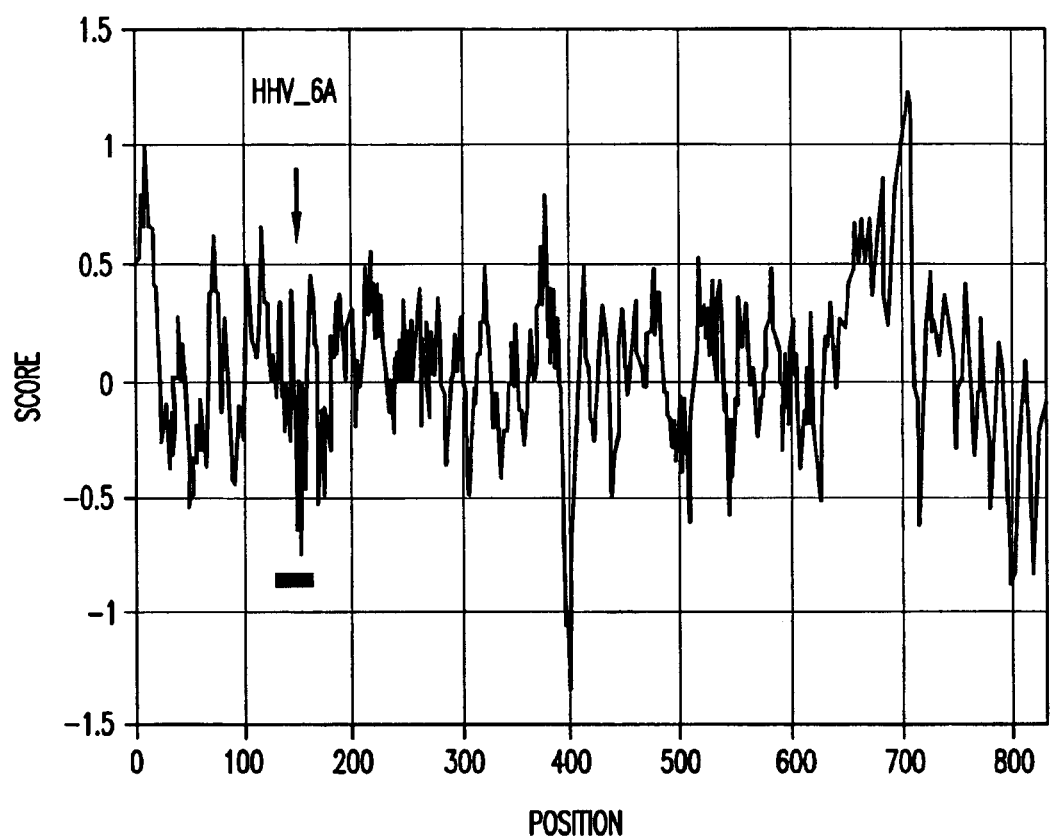
Figure 1C:
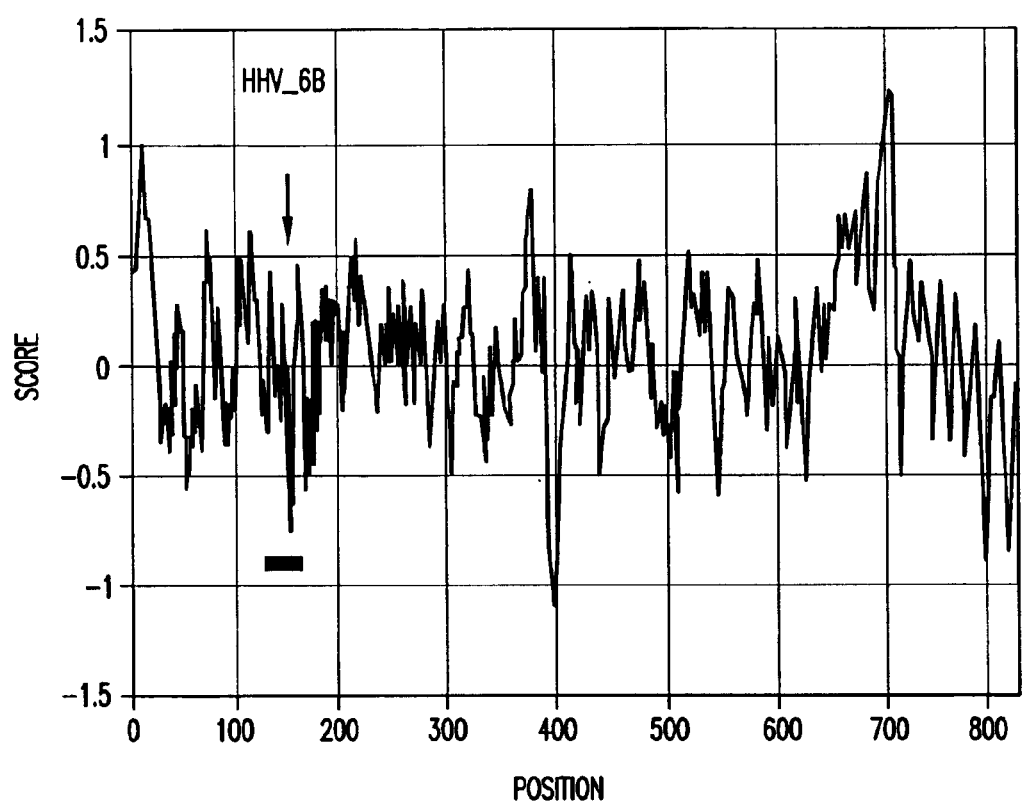
Figure 1D:
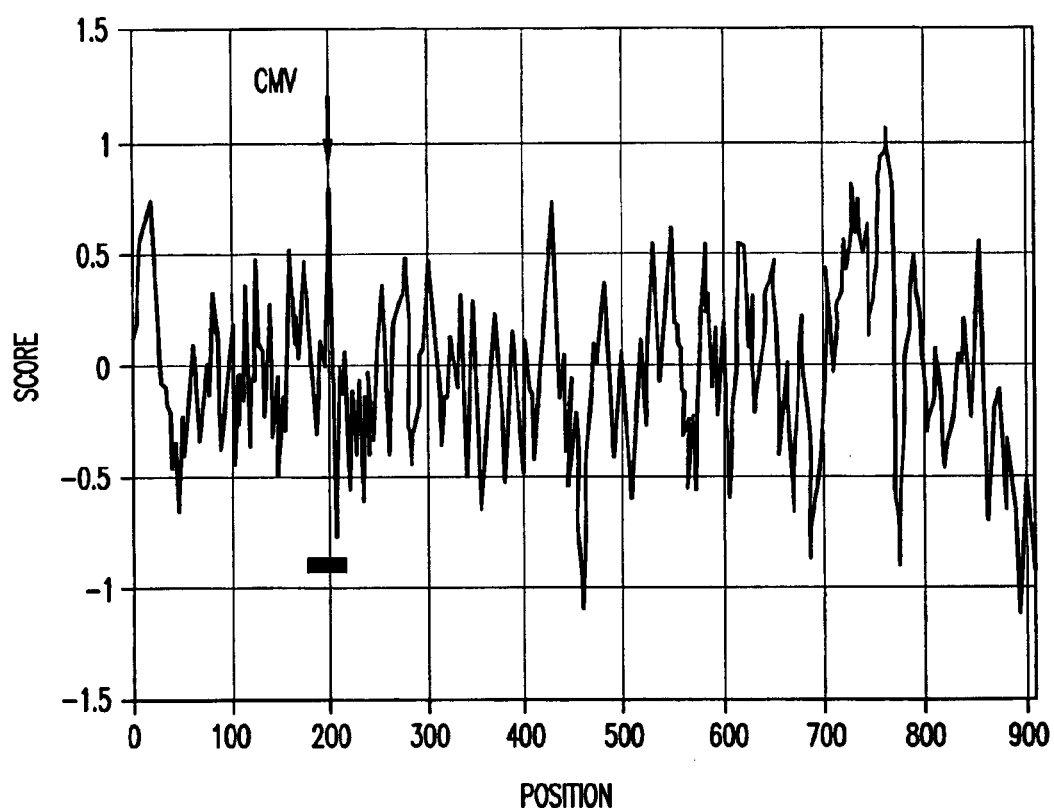

This region of 24 amino acids offers the advantage of being in the N-terminal quarter of the protein and thus of being exposed to the outside of the molecule because of its hydrophilicity. This exposed region is found in the position that is substantially homogeneous with the other β-herpesviruses (HHV-6A, HHV-6B, CMV) (FIG. 1).

Figure 2A:
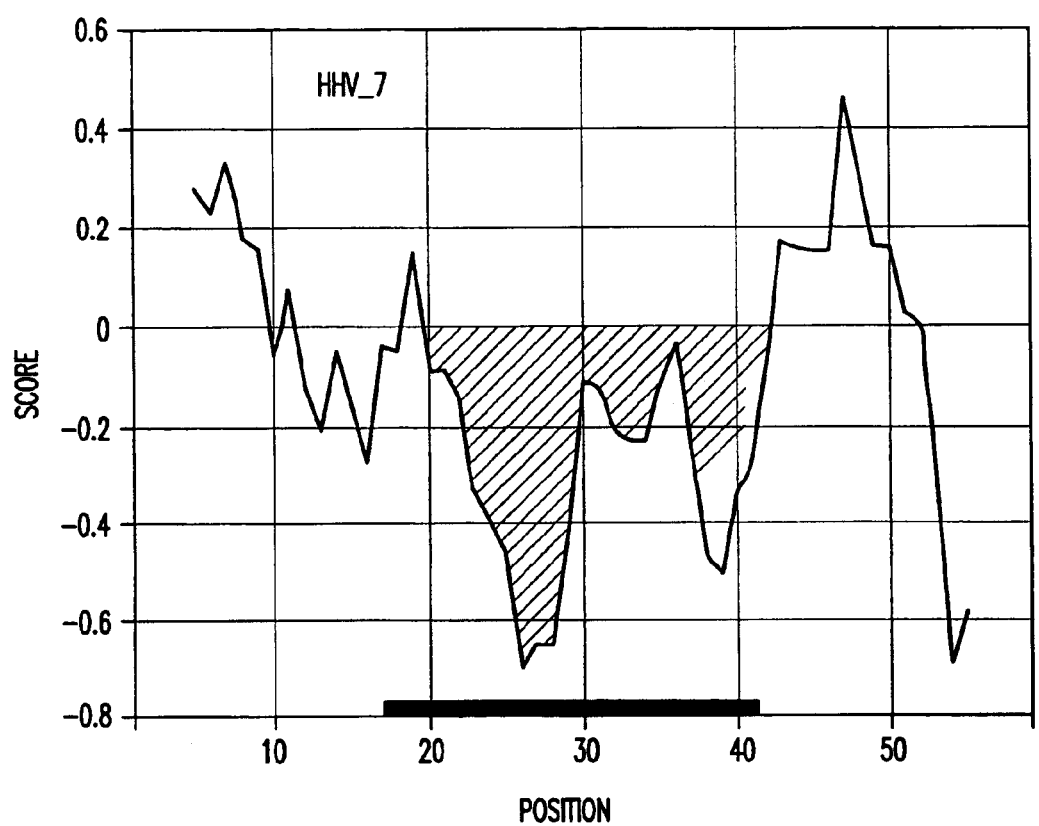
FIG. 2 shows a higher resolution study of the hydrophilicity of the selected region, the H7GB 129–152 peptide being shown as the black line.
Figure 2B:
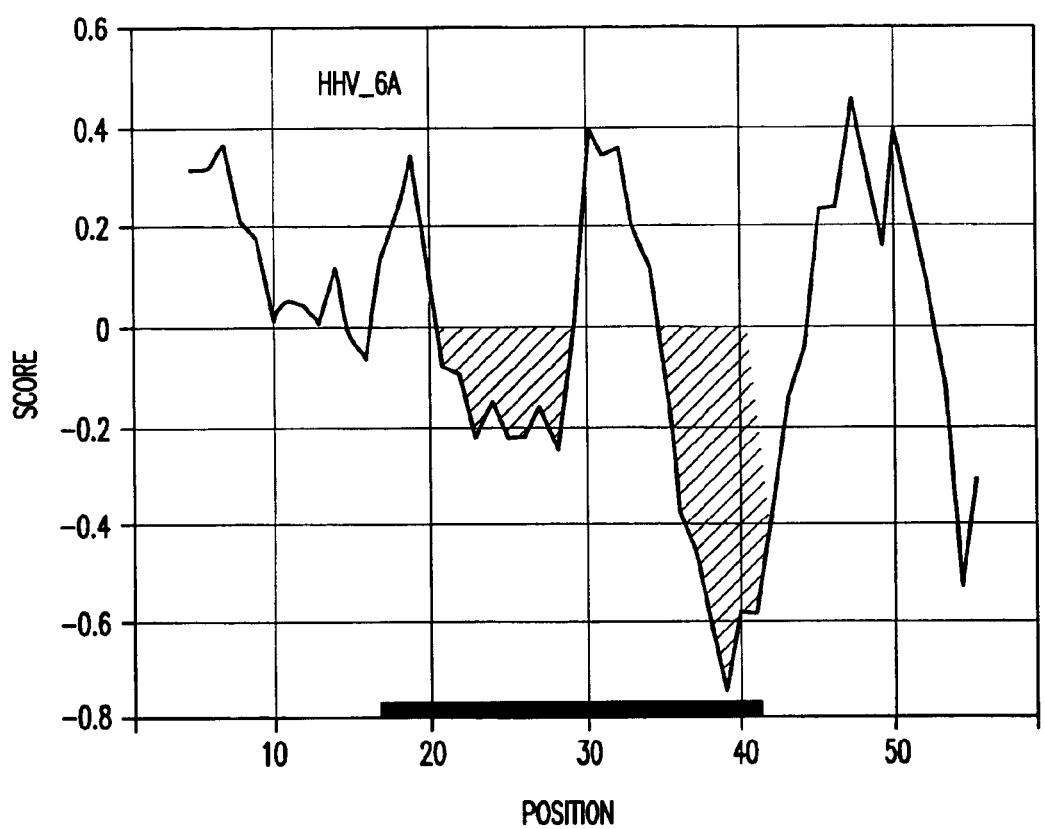
Figure 2C:
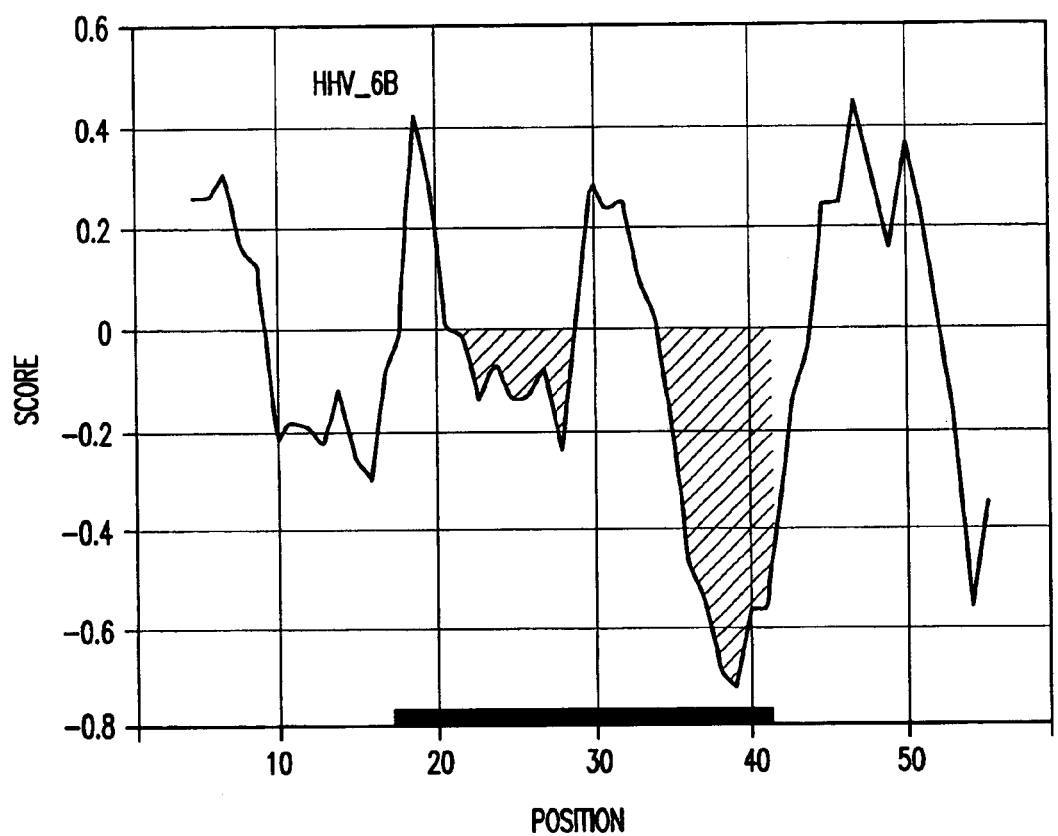
Figure 2D:
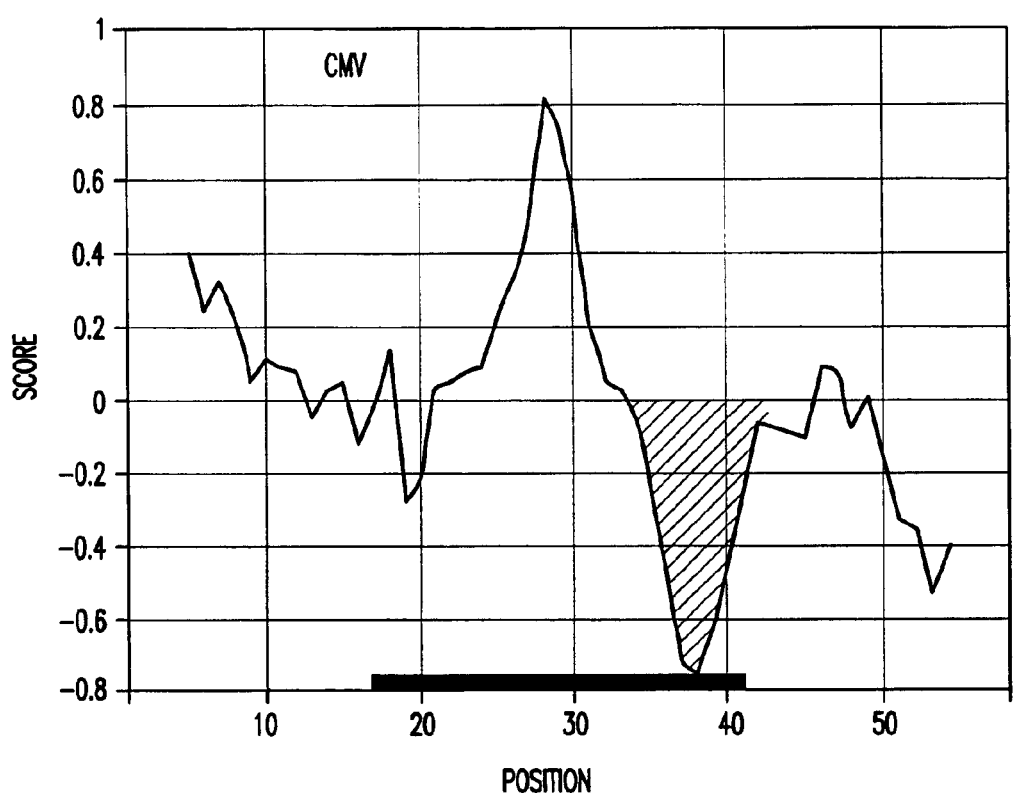

A higher resolution study of the hydrophilicity of the selected region shows, however, after alignment of the sequences, that the hydrophilicity peak of HHV-7 does not occupy exactly the same position as those of HHV-6A, HHV-6B, and CMV (FIG. 2). A study of the protein sequence, again after alignment (FIG. 3), confirms that HHV-7 has a highly hydrophilic original sequence centred on residues 136–141 in the selected region of the peptide:

Arg-Ser-Glu-Glu-Glu-Glu (RSEEEE) (SEQ ID NO: 2).

This sequence is not found in other β herpesviruses. In order that this motif, which most probably represents all or a portion of the dominant epitope or epitopes, is present and correct after adsorption onto a solid support, bordering sequences have been joined to said particular sequence to produce the total sequence of the above H7GB 129–152 peptide.

It should be noted that this peptide contains, at its C-terminal end, a motif Asp-Glu-Tyr-Val-Asn, which is a priori highly hydrophilic, which can also behave as an epitope as regards anti-gB antibodies. However, it is improbable that this region at the free end of the peptide could adopt a configuration conducive to behaving as a linear epitope. Further, the Asn terminal residue can be a gB N-glycosylation site as it belongs to a canonical sequence Asn-X-Thr which is well conserved in the four β-herpesviruses. The steric hindrance caused by glycosylation (if it exists) probably would oppose exposure of the Asp-Glu-Tyr-Val-Asn motif as an epitope on the surface of the molecule.

Thus, the present invention concerns immunogenic peptides comprising at least six consecutive amino acids from a hydrophilic region of the glycoprotein B (gB) of human herpesvirus 7 (HHV-7) and reacting in a specific manner with antibodies directed against HHV-7. The term "reacting specifically with antibodies directed against HHV-7" means that antibodies directed against β-herpesviruses other than HHV-7 (for example against HHV-6) do not have a particular affinity for said peptides.

Preferably, the amino acids sequence of the gB present in the peptides of the invention derive from the N-terminal region of said protein.

In a preferred implementation of the peptides of the invention, their sequence comprises the motif Arg-Ser-Glu-Glu-Glu-Glu (SEQ ID NO: 2). More preferably, a peptide of the invention is characterized in that it comprises the sequence Ser-Val-Lys-Arg-Ser-Glu-Glu-Glu-Glu-Tyr-Val-Ala (SEQ ID NO: 3), if necessary modified by one or more amino acid substitutions. Any modifications to said sequence will be made so that the presentation of the motif Arg-Ser-Glu-Glu-Glu-Glu (SEQ ID NO: 2) will always permit its interaction with anti-HHV-7 antibodies. In particular, the amino acids can be substituted with amino acids with an analogous hydrophilicity.

The peptides of the invention preferably comprise 15 to 25 amino acids, but this is not limiting in nature.

A particular peptide of the invention is the H7GB 129–152 peptide corresponding to amino acids 129 to 152 of gB and defined by the peptide sequence: Leu-Ser-Ser-Ile-Ser-Val-Lys-Arg-Ser-Glu-Glu-Glu-Glu-Tyr-Val-Ala-Tyr-His-Lys-Asp-Glu-Tyr-Val-Asn (SEQ ID NO: 1). or more conservative amino acid modifications, provided that the immunological reactivity of said peptide is not modified.

The peptides of the invention as described above can also be modified by adding one or more terminal amino acids that are heterologous to gB to one end or to both ends. If appropriate, said peptides can also be labeled.

The eight human serums tested as described above by Western blot were used to determine the best reactivity conditions for said peptide in an ELISA system (Example 1 below). The following can be defined (optical density):

mean value of the background noise to the reaction: 0.09;

mean value of the results obtained with negative serums: 0.18;

a positivity threshold of 0.23, corresponding to the mean of negatives increased by 2 standard deviations (error risk of 5%) or 0.25, corresponding to the mean of negatives increased by 3 standard deviations (error risk of less than 1%);

a spectrum of positive serum values of 0.4 to 1.1.

The reproducibility of the results was shown to be highly satisfactory, both when comparing separate experiments carried out simultaneously (intra-test variability study) and with separate experiments carried out on different days (inter-test variability study). The specificity of the results as regards the peptide used was verified in several ways:

test for positive HHV-7 serums towards a further non pertinent viral peptide (HHV-8 peptide) under the same conditions or in the absence of any peptide fixed in the reaction wells: the reactions are always under the positivity threshold (Example 2 below);

test for positive HHV-7 serums towards a HHV-7 peptide after adsorbing the serums on different extracts from infected cells: the positivity signal is significant reduced or even disappears when cells are infected with HHV-7 but conserved or only slightly modified when the cells are infected with CMV and HHV-6 (Example 3 Below);

absence of reactivity with six seronegative HHV-7 serums (Example 4 below);

inhibiting action of soluble peptide brought into contact in advance with serums, on ELISA reactivity by a dose-dependent competition phenomenon (Example 5 below).

It should be noted that the present invention is not in any case limited to the H7GB 129–152 peptide described above. In contrast, any peptide comprising a region that is homologous with the HHV-7 gB protein and which has immunological properties similar to those of H7GB 129–152 (i.e., reacting in a specific manner with antibodies directed against HHV-7), is also encompassed in the scope of the present invention. Means for determining whether a peptide falls within the scope of the present invention are described in the examples.

In particular, a peptide carrying the residues Arg-Ser-Glu-Glu-Glu-Glu (SEQ ID NO: 2), surrounded by amino acids that are partially or totally heterologous to gB, can react specifically with antibodies directed against HHV-7, provided that they are correctly presented. The influence of inserting or deleting residues surrounding the Arg-Ser-Glu-Glu-Glu-Glu (SEQ ID NO: 2) motif on the immunological properties of the peptide obtained are difficult to predict if the total charge of the peptide and the polarity of the modified residues are conserved overall. In all cases, only synthesis of a novel peptide and its testing (for example, by ELISA as described in Example 1) will allow the functional effect of any modifications to be accurately determined.

The properties of the peptides of the invention thus allow them to act as a basis for the development of a specific serological test the indications for which should be, inter alia:

monitoring and studying HHV-7 infections in children at the time of primary phase infection (1–3 years);

serological monitoring of immunodepressed subjects with the idea of correlating modifications to the serological reactivity to the degree of dysfunction of the immune system;

demonstrating a correlation between the titer of the anti-gB antibodies and the capacity to control HHV-7 infection;

a clear distinction between HHV-7 and HHV-6 infections from certain particular clinical manifestations connected with primary phase infection and in general seroprevalance studies;

determining the HHV-7 serology of a candidate for an organ graft and a potential organ donor for use in grafts.

The present invention also concerns a kit for the specific diagnosis of HHV-7, comprising a peptide as described above. If appropriate, said peptide can be fixed on a support. Preferably, a diagnostic kit of the invention also comprises a detectable antibody directed against one or more classes of human immunoglobulins. This detectable antibody may be radio-labelled, fluorescent, or bound to an enzyme. In the case in which the detectable antibody is bound to an enzyme, the kit advantageously comprises a substrate for said enzyme which allows a visually detectable result to be produced.

The peptides of the invention can also be used in the composition of more complex diagnostic kits which, in addition to specifically detecting an HHV-7 infection, enable serodiagnosis of a sample as regards one or more other β-herpesviruses to be carried out.

The invention also provides a method for serological detection of HHV-7 in a biological sample, comprising a step for bringing said biological sample into contact with a peptide as hereinbefore described, and a step for determining bonding of the peptide with any antibodies that may be present in the sample. In such a method, the step for determining bonding of the peptide with any antibodies that may be present in the sample can be carried out using any method that is accessible to the skilled person for identifying a specific bond between an antigen and an antibody, in particular using an ELISA test, chemiluminescence, by fixing onto a micro- or macro-array type support, by immunofluorescence, by radio-immuno-labelling, by agglutination or by haemagglutination.

Further, the immunological properties of the peptides described above constitute particularly interesting candidates for forming part of the composition of immunogenic preparations intended to encourage an immune response against HHV-7 in a subject. Said preparations can be complex and may comprise other antigens, in particular the major antigens of HHV-7 or possibly of other β-herpesviruses. The invention thus also concerns an immunogenic preparation intended to encourage an immune response against HHV-7, characterized in that it comprises at least one peptide at least one region of which derives from gB, as described above.

Finally, the invention concerns the use of a peptide in accordance with the invention in preparing a pharmaceutical composition for the serological detection of HHV-7, the diagnosis of HHV-7 in a subject, or stimulation of an immune response directed against HHV-7 in a subject.

The following examples and figures provide non-limiting illustrations of certain advantages and features of the present invention.

EXAMPLE 1

Determination of Optimum Conditions for the Reactivity of the H7GB 129–152 Peptide in an ELISA System A variety of concentrations of peptide (0.1 to 5 µg/ml) were used when fixing to the bottom of reaction wells, along with different dilutions of human serum during an ELISA test. The conditions judged to be the best were a peptide concentration of 0.5 µg/ml and a serum dilution of 1/100. However, other conditions, including modifications to the other reagents, could result in better performing tests.

EXAMPLE 2

Test for Positive HHV-7 Serums Towards Another Non-Pertinent Viral Peptide (HHV-8 Peptide) in an ELISA System with the H7GB 129–152 Peptide Eight reference serums seropositive for HHV-7, labeled P1 to P8, were tested in the absence of the peptide and against a HHV-8 peptide that had no homology with H7GB 129–152. The results (summarized in the table below) of the optical density indicate an absence of a significant reactivity under these conditions (positivity threshold for the reaction corresponded to an OD of 0.25).

| peptide used | OD as a function of the serum tested | | | | | | | |
|---|---|---|---|---|---|---|---|---|
| for ELISA | P1 | P2 | P3 | P4 | P5 | P6 | P7 | P8 |
| no peptide | 0.05 | 0.08 | 0.07 | 0.06 | 0.06 | 0.06 | 0.05 | 0.04 |
| HHV-8 peptide | 0.13 | 0.16 | 0.17 | 0.15 | 0.15 | 0.14 | 0.16 | 0.14 |
| H7GB 129–152 | 1.11 | 0.56 | 0.96 | 0.60 | 0.69 | 1.01 | 0.64 | 0.88 |

EXAMPLE 3

Test in an ELISA System Using H7GB 129–152 Peptide from Positive HHV-7 Serums Towards H7GB 129–152 Peptide, After Adsorption of Serums onto Different Infected Cell Extracts The eight human serums P1 to P8 were adsorbed with different extracts from cells infected or otherwise prior to being tested using ELISA towards the H7GB 129–152 peptide under pre-established conditions. The results are expressed as a percentage reduction compared with the signal obtained in the absence of any pre-adsorption (see Example 2). The results summarized below indicate that only pre-adsorption with cells expressing HHV-7 gB could significantly reduce the signal.

| preadsorption | | percentage reduction in OD (%) | | | | | | | |
|---|---|---|---|---|---|---|---|---|---|
| cells | infection | P1 | P2 | P3 | P4 | P5 | P6 | P7 | P8 |
| SupT1 | none | 5 | 29 | 0 | 11 | 20 | 0 | 11 | 17 |
| SupT1 | HHV-7 | 40 | 58 | 56 | 52 | 50 | 43 | 40 | 56 |
| Sf21 | none | 11 | 22 | 0 | 0 | 17 | 0 | 0 | 0 |
| Sf21 | Baculovirus expressing HHV-7 gB | 46 | 66 | 30 | 26 | 57 | 26 | 60 | 42 |
| MT4 | none | 20 | 2 | 4 | 10 | 13 | 7 | 11 | 0 |
| MT4 | HHV-6 | 11 | 0 | 11 | 3 | 19 | 6 | 0 | 0 |
| FH | none | 18 | 0 | 13 | 0 | 9 | 13 | 0 | 6 |
| FH | CMV | 20 | 5 | 8 | 0 | 11 | 2 | 3 | 0 |

EXAMPLE 4

Test in an ELISA System Using H7GB 129–152 Peptide from Six Seronegative HHV-7 Serums Six reference serums designated N1 to N6 which were seronegative for HHV-7 but had a very high titer of anti-HHV-6 antibodies (>1280) were tested. The results show a low reactivity to the peptide. As for the seropositive serums, they also show a variability, expressed in the form of a coefficient of variability (CV), which was sufficiently low to envisage development of a routine ELISA test.

| test serum | mean OD | SD | coefficient of variability (%) | |
|---|---|---|---|---|
| | | | intra-test | inter-test |
| N1 | 0.20 | 0.02 | 9.5 | 8.8 |
| N2 | 0.16 | 0.02 | 8.3 | 13.8 |
| N3 | 0.18 | 0.01 | 3.3 | 3.6 |
| N4 | 0.17 | 0.02 | 11.0 | 11.0 |
| N5 | 0.18 | 0.01 | 13.2 | 4.8 |
| N6 | 0.16 | 0.07 | 44.7 | 47.0 |

EXAMPLE 5

Inhibiting Action of Soluble Peptide, Previously Brought into Contact with Serums, on ELISA Reactivity Positive serums P1 to P8 were pre-incubated in the presence of soluble H7GB 129–152 at two different concentrations then tested using ELISA. The reduction in the signal with respect to the same non incubated serums results from the competition exerted by the soluble peptide towards anti-HHV-7 antibodies.

| concentration of H7GB 129–152 | percentage OD reduction (%) | | | | | | | |
|---|---|---|---|---|---|---|---|---|
| during pre-incubation (µg/ml) | P1 | P2 | P3 | P4 | P5 | P6 | P7 | P8 |
| 5 | 27 | 30 | 32 | 48 | 14 | 23 | 37 | 24 |
| 50 | 75 | 45 | 66 | 61 | 70 | 67 | 63 | 61 |

REFERECES

Franti M, Aubin J T, Poirel L, Gautheret-Dejean A, Candotti D, Huraux J M and Agut H. Definition and distribution analysis of glycoprotein B gene alleles of human herpesvirus 7. J Virol 1998; 72: 8725–30.

Franti M, Aubin J T, Gautheret-Dejean A, Malet I, Cahour A, Hufaux J M and Agut H. Preferential associations of alleles of three distinct genes argue for the existence of two prototype variants of human herpesvirus 7. J Virol 1999, 73: 9655–58.

Nicholas J. Determination and analysis of the complete nucleotide sequence of human herpesvirus 7. J Virol 1996: 70: 5975–89.

Megaw A G, Rapaport D, Avidor B, Frenkel N, Davison A J. The DNA sequence of the RK stain of human herpesvirus 7. Virology 1998; 244: 119–32.

What is claimed is:

1. An immunogenic peptide comprising at least six consecutive amino acids from a hydrophilic region of the glycoprotein B (gB) of human herpesvirus 7 (HHV-7) and reacting in a specific manner with antibodies directed against HHV-7, wherein said inmunogenic peptide consist essentially of the peptide sequence:

Leu-Ser-Ser-Ile-Ser-Val Lys-Arg-Ser-Glu-Glu-Glu-Glu-Tyr-Val-Ala-Tyr-His-Lys-Asp-Glu-Tyr-Val-Asn (SEQ ID NO: 1) or a peptide sequence of SEQ ID NO: 1, which is modified by conservative substitution(s) which do not alter the immunological reactivity of said peptide.

2. The peptide according to claim 1, wherein the amino acid sequence of the gB present in the peptides of the invention are from the N-terminal region of said protein.

3. The peptide according to claim 1, wherein said peptide sequence consists essentially of the sequence Arg-Ser-Glu-Glu-Glu-Glu (SEQ ID NO:2).

4. The peptide according to claim 1 wherein said peptide consists essentially of the sequence Ser-Val-Lys-Arg-Ser-Glu-Glu-Glu-Glu-Tyr-Val-Ala (SEQ ID NO: 3); or a peptide sequence of SEQ ID NO: 3 which is modified, by conservative modification(s) that do not alter the immunological reactivity of said peptide.

5. The peptide according to claim 1 comprising 15 to 25 amino acids.

6. The peptide according to claim 1, further comprising one or more terminal amino acids that are heterologous to gB, which do not alter the immulogical reactivity of said peptide.

7. An immunogenic preparation for encouraging an immune response against HHV-7 comprising at least one peptide according to claim 5, and a suitable carrier.

8. Immunogenic preparation for encouraging an immune response against HHV-7 comprising at least one peptide according to claim 6 and other antigens of HHV-7.

* * * * *